United States Patent
Luque et al.

(10) Patent No.: US 6,726,357 B2
(45) Date of Patent: Apr. 27, 2004

(54) MEDIA IDENTIFICATION SYSTEM

(75) Inventors: Phillip R. Luque, Boise, ID (US); Jeffrey S. Weaver, Ft. Collins, CO (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 0 days.

(21) Appl. No.: 10/151,412

(22) Filed: May 20, 2002

(65) Prior Publication Data

US 2003/0214995 A1 Nov. 20, 2003

(51) Int. Cl.[7] .............................................. G01N 25/00
(52) U.S. Cl. ....................... 374/45; 374/179; 374/153; 374/120; 374/137
(58) Field of Search ................ 374/179, 153, 374/120, 137, 43, 45, 141; 400/703; 399/45; 194/303, 212

(56) References Cited

U.S. PATENT DOCUMENTS

| | | | | |
|---|---|---|---|---|
| 4,644,163 A | * | 2/1987 | Selander | 250/341.6 |
| 5,056,929 A | * | 10/1991 | Watanabe et al. | 374/181 |
| 5,127,643 A | | 7/1992 | DeSanctis et al. | |
| 5,130,757 A | * | 7/1992 | Ito | 399/14 |
| 5,138,178 A | | 8/1992 | Wong et al. | |
| 5,806,992 A | | 9/1998 | Ju | |
| 5,905,925 A | * | 5/1999 | Kawabata et al. | 399/45 |
| 5,939,646 A | | 8/1999 | Fowler | |
| 5,962,861 A | | 10/1999 | Fowler | |
| 6,028,318 A | | 2/2000 | Cornelius | |
| 6,034,360 A | * | 3/2000 | Karlsson | 219/553 |
| 6,047,110 A | * | 4/2000 | Smith | 358/1.12 |
| 6,157,791 A | | 12/2000 | Haines et al. | |
| 6,163,662 A | * | 12/2000 | Martin et al. | 399/45 |
| 6,386,676 B1 | * | 5/2002 | Yang et al. | 347/19 |
| 6,389,241 B1 | * | 5/2002 | Cernusak et al. | 399/44 |
| 6,393,227 B1 | * | 5/2002 | Weaver et al. | 455/423 |
| 6,597,877 B1 | * | 7/2003 | Luque | 399/45 |

FOREIGN PATENT DOCUMENTS

| | | | | |
|---|---|---|---|---|
| EP | 1070597 | | 1/2001 | |
| JP | 05046841 A | * | 2/1993 | G07D/7/00 |
| JP | 06266925 A | * | 9/1994 | G07D/7/00 |

* cited by examiner

*Primary Examiner*—Diego Gutierrez
*Assistant Examiner*—Lydia M. De Jesús

(57) ABSTRACT

The present invention involves identifying media type in a media processing device. A system according to one embodiment of the invention includes a thermal energy source and a thermal energy sensor. The thermal energy source and thermal energy sensor are arranged along a media feed path so as to accommodate transfer of thermal energy to the media by the thermal energy source, diffusion of such thermal energy, and subsequent sensing of such diffused thermal energy to determine a heat capacity of the media, such heat capacity being indicative of media type.

5 Claims, 2 Drawing Sheets

MEDIA IDENTIFICATION SYSTEM

BACKGROUND

Media processing devices, such as laser printers and media sorters, among others, may operate on various types of media, such as various papers or plastics. Printable papers might include wood-and cotton-based materials of different qualities, of virgin and/or recycled content, formed in different thicknesses, and with different surface treatments. Printable plastics may include similar variations, in both transparent and opaque forms.

For any given printer, the quality of text and images printed on various media may be dependent on a number of factors, not the least of which is media type. By adjusting the print process based on media type, print quality may be improved. For laser printers, in particular, it may be advantageous to adjust fusing speed based on the type of media, often expressed in terms of media weight. One method of identifying media weight involves measuring the thickness of the media, thickness generally being indicative of media weight. Typically, this is done using an inductive or eddy current sensor that touches the media as it passes through the printer. The sensor and its circuitry produce a signal that varies as a function of the distance between the sensor and a metal plate that underlies the media. Capacitive sensors have been proposed to measure thickness as well.

However, thickness may not be the best measure of media type or media weight due to the different types of materials that may be employed in producing media. Furthermore, thickness sensors typically are fragile and expensive, and may be subject to wear, as they often are in contact with the media as it is fed by, to, or within a media processing device.

SUMMARY

The present invention involves identifying media type in a media processing device. A system according to one embodiment of the invention includes a thermal energy source and a thermal energy sensor. The thermal energy source and thermal energy sensor are arranged along a media feed path so as to accommodate transfer of thermal energy to the media by the thermal energy source, diffusion of such thermal energy, and subsequent sensing of such diffused thermal energy to determine a heat capacity of the media, such heat capacity being indicative of media type.

DETAILED DESCRIPTION OF THE INVENTION

Figure 1:
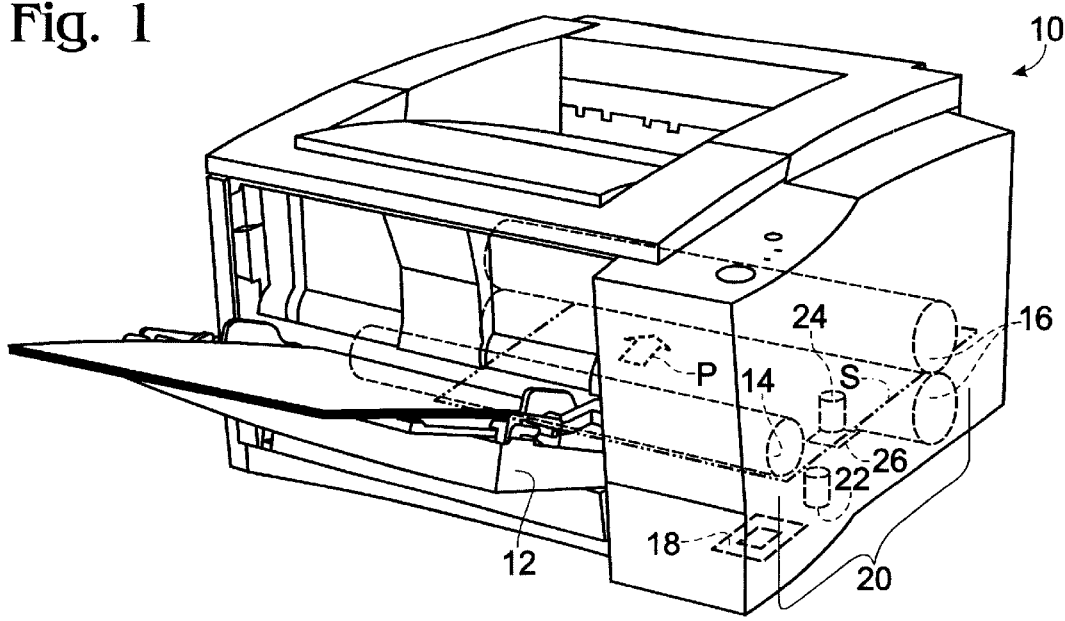
FIG. 1 is an isometric view of a printer incorporating an embodiment of a media identification system.

Referring to FIG. 1, a print-media processing device is depicted in the form of a printer 10. For the sake of simplicity, the embodiments discussed herein will be described in the context of printer 10. However, it will be appreciated that these embodiments may take other forms, and be used in connection with any number of media processing devices, including copiers, facsimile machines and media sorters, among others.

Printer 10 may include a media tray 12, a feed roller 14 and a toner fuser 16. Feed roller 14 may feed a media sheet S along a feed path P, as indicated by arrow P. Feed path P may be defined as the path media such as media sheet S travels along while being fed through printer 10. Therefore, feed path P may be delineated by the width of media sheet S. The speed of toner fuser 16 and other operational characteristics of the components of printer 10 may be controlled by a processor such as microprocessor 18, typically based on the type of media as determined by the media identification system described herein.

Accordingly, it will be noted that printer 10 may further include a media system 20, incorporating a thermal energy source 22 and a thermal energy sensor 24. An optional reference surface 26 also may be provided for use in determining ambient temperature as will be described further below. As indicated, thermal energy source 22 and thermal energy sensor 24 may be arranged along feed path P so that media sheet S must first pass by energy source 22, where thermal energy is applied, and then pass by energy sensor 24 where the resulting media temperature is sensed. In the depicted embodiment, thermal energy source 22 and thermal energy sensor 24 are disposed on opposite sides of the media path so as to provide for increased differentiation in the sensed temperature for differing media types. Alternatively, energy source 22 and energy sensor 24 may both be oriented above feed path P, or both be oriented below feed path P. Where a reference surface, such as reference surface 26, is employed, such reference surface typically is placed on an opposite side of the feed path from energy sensor 24 so that the reference surface may be sensed by the energy sensor, but not interfere with monitoring of temperature of media passing along feed path P.

Figure 2:
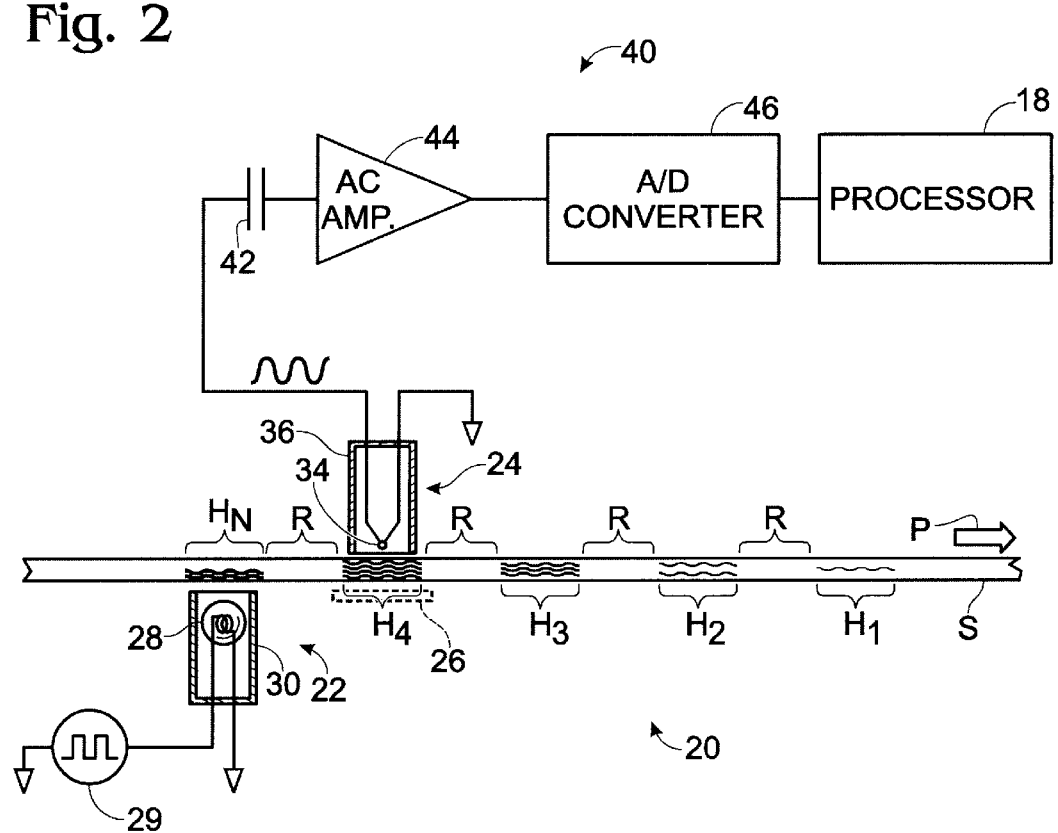
FIG. 2 is a somewhat schematic side elevation view showing the media identification type determination system of FIG. 1.

Referring now to FIG. 2, a somewhat schematic side elevation view of system 20 is provided so as to more clearly illustrate operation of the thermal energy source and thermal energy sensor in concert. As indicated, thermal energy source 22 may include a radiant heat source 28, which may take the form of an infrared heat source, such as an incandescent light bulb, light-emitting diode, or any other suitable heat-generating device. It will be appreciated that other types of thermal energy sources may be used, including cooling devices, and that the invention is not limited to the use of a heat source. Furthermore, it is to be noted that heat source 28 may be disposed within a shield 30, which is shown in sectional view in FIG. 2. Shield 30 may be configured to direct thermal energy generated by heat source 28 toward feed path P, and specifically towards media sheet S.

Thermal energy thus may be transferred to media sheet S by heat source 28 of thermal energy source 22. Correspondingly, media sheet S will typically absorb the thermal energy, and diffuse such thermal energy through the media sheet until the temperature is substantially uniform through the media sheet. As will be appreciated by those skilled, the rate of diffusion and the amount of thermal energy that media sheet S is capable of storing is related to the heat capacity of the media sheet. Heat capacity, in turn, is related to media weight and thus to media type. As indicated in FIG. 2 (by horizontal lines in the media designating heat), a portion (or patch) of media sheet S may become thermally stable within a few hundred milliseconds, typically as the media passes by thermal energy source 22 and on to the thermal energy sensor 24.

In one embodiment of the invention, thermal energy source 22 may be powered by a pulsed drive mechanism 29, which may be configured to apply power to heat source 28 as a square wave. This, in turn, may result in pulsing of the radiant heat source so as to produce interleaved heated patches ($H_1$, $H_2$, $H_3$, $H_4$, ... $H_N$) and unheated reference patches (R) on a media sheet S. Such heated patches, it will be appreciated, will diffuse heat in accordance with the heat capacity of the media. Heavier media types, for example, typically will have a higher heat capacity than lighter weight media. Therefore, for a given amount of applied thermal energy, and upon a given amount of elapsed time (during which the media may become thermally saturated), heavier media typically will be cooler than would lighter weight media. In FIG. 2, applied thermal energy may be predicted based on the input to pulsed drive mechanism 28, and elapsed time may be predicted based on the media feed rate and the distance between energy source 22 and energy sensor 24. Temperature thus may be sensed by thermal energy sensor 24, and used to determine media weight, as will be described further below.

Referring still to FIG. 2, it will be noted that thermal energy sensor 24 is spaced downstream from thermal energy source 22, and thus is configured to sense temperature of media upon predictable passage of the media past the thermal energy sensor. Thermal energy sensor 24 thus may include a temperature-sensing device 34 capable of sensing temperature of media within its sensing view, and to report such temperature as an output voltage. Temperature-sensing device 34 may take the form of a thermocouple device, a semiconductor device, or any other apparatus capable of sensing temperature, or relative temperature. Where thermal energy is pulsed, as shown in FIGS. 1 and 2, the temperature-sensing device may take the form of a passive infrared (PIR) sensor, or a polyvinylidene fluoride (PVDF) sensor, both of which sense dynamic changes in temperature rather than static temperature. In any event, by comparing the sensed temperature to a reference temperature (whether stored in memory, sensed separately, or inherent in the second temperature data), it is possible to determine heat capacity of the media, and thus, media weight and media type.

In operation, thermal energy thus typically is applied to a patch of media sheet S by thermal energy source 22 as the media sheet passes along feed path P. After such thermal energy has been applied, the heated patch of media sheet S passes downstream along the feed path to thermal energy sensor 24. The thermal energy is diffused during such passage downstream, typically in accordance with a heat capacity of the media. Thermal energy sensor 24 thus may sense the amount of thermal energy radiated from media sheet S, typically by sensing temperature opposite the surface of media sheet S to which thermal energy was applied by thermal energy source 22. To aid in this temperature sensing, temperature-sensing device 34 may be disposed within a shield 36 (shown in sectional view) which directs thermal energy radiated from feed path P, such as from media sheet S, toward temperature-sensing device 34. By comparing this sensed temperature with a reference temperature (typically, ambient temperature), a heat capacity of media sheet S may be determined, for example, via a look-up table, in calculation, or the like. Correspondingly, a media type and/or weight may be determined based on such heat capacity, again, via a look-up table, calculation, or the like.

As indicated, pulsing the thermal energy source may result in unheated reference patches (designated R) intermediate the heated patches, any one of which may be sensed to determine a reference temperature for use in comparing with the sensed temperature of the heated patch to determine heat capacity of the media. Where the temperature-sensing device remains active, such reference patches interleaved with heated patches may provide a sinusoidal temperature-sensor output accommodating potentially simpler detection and interpretation of heat capacity data. Alternatively, thermal energy source 22 may remain active so as to provide a thermally affected media strip (not shown). In this non-pulsing heat source configuration, a reference surface 26 may be placed in thermal view of the temperature-sensing device to serve as a reference for measurement of ambient temperature prior to or subsequent to passage of the media sheet thereby. This ambient temperature may be used as the reference temperature to which the sensed temperature of the heated media strip may be compared in determining heat capacity of the media.

Where an ambient temperature measurement is being made (that is, where sensed ambient temperature is being compared to a sensed temperature of a heated portion of media sheet S to which thermal energy has been applied), it may be desirable that reference surface 26 have similar thermal emissivity characteristics to a typical media sheet S. Emissivity of an object, or physical body, may be defined as the ratio of the body's thermal radiance compared to that of a perfect blackbody (a body having one hundred percent thermal radiance) at the same temperature. Thus, emissivity is a measure of the thermal radiation and absorption efficiency of a body. For a perfect blackbody, emissivity equals 1.0. Most media have emissivity values near 1.0 in the infrared spectrum, and are typically greater than 0.9. Therefore, a reference surface 26 having an emissivity of greater than 0.9 may be desirable to allow for more accurate determinations of heat capacity.

In FIG. 2, where the thermal energy source is pulsed so as to provide heated patches interleaved with reference patches, a heat capacity determination system 40 is depicted schematically for use in connection with such a thermal energy source. As shown, heat capacity determination system 40 may include thermal energy sensor 24, which typically produces a sinusoidal voltage output based on variations in the sensed temperature of media sheet S. These variations, it will be appreciated, are due to interleaving of heated patches with non-heated patches on media sheet S by pulsing thermal energy source 22. As further indicated, the output of the thermal energy sensor is passed through a DC blocking capacitor 42, through an AC amplifier 44, and through an analog-to-digital (A/D) converter 46 to processor 18. Processor 18, based on the voltage data from A/D converter 46, may perform a root-mean-square (RMS) calculation to produce a value representative of heat capacity of the media, and thus representative of media weight and media type. Such value typically will correspond to the root-mean-square of voltages representing the sensed temperatures of each heated patch ($H_1$–$H_N$) (where N is the number of heated patches sampled). Such heated patches may extend substantially along the entirety of the media sheet, or along some portion capable of providing meaningful data.

Heat capacities determined using system 40 may be used to modify the operation of media processing devices, as has been previously described. For example, processor 18 may control the speed of fuser 16 in printer 10 based on a determined media type and/or weight. In other media processing devices, processor 18 may control other functions that may depend on heat capacity, media weight and/or media type (such as selecting output locations in a media sorter).

Figure 3:
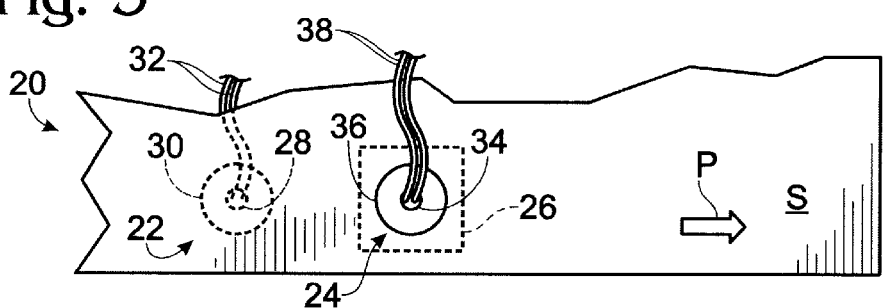
FIG. 3 is a plan view showing the media identification type determination system of FIG. 2.

FIG. 3 is a plan view of media identification system 20 showing thermal energy source 22 (heat source 28 disposed within shield 30) in line, along feed path P, with thermal energy sensor 24 (temperature-sensing device 34 disposed within shield 36). As indicated, optional reference surface 26 may be located concentrically below thermal energy sensor 24, and on an opposite side of feed path P from thermal energy source 22. From this perspective, it will be appreciated that a heated patch will pass downstream from thermal energy source 22 to thermal energy sensor 24 for sensing of the temperature of the heated patch after predictable diffusion of the applied thermal energy.

Figure 4:
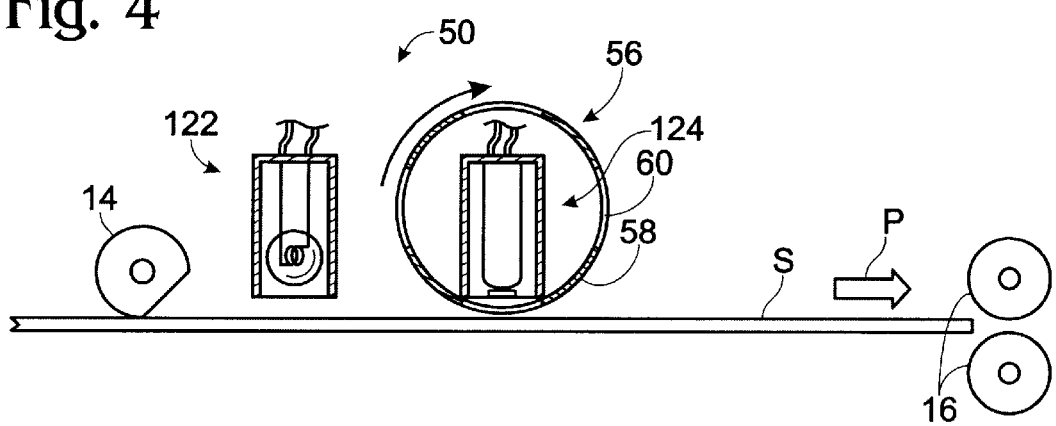
FIG. 4 is a fragmentary side elevation view showing an alternative embodiment media identification system as it may be used in connection with the printer of FIG. 1
Figure 5:
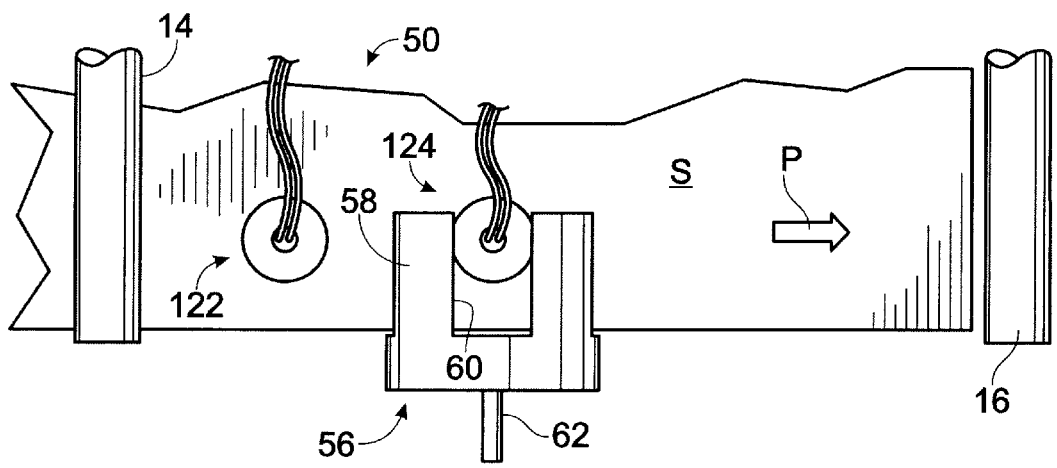
FIG. 5 is a fragmentary plan view showing the media identification system of FIG. 5.

Referring now to FIGS. 4 and 5, an alternative media identification system 50 is depicted in somewhat similar fashion to FIGS. 2 and 3, but also showing feed roller 14 and fuser 16. System 50, however, differs from system 20 in that both thermal energy source 122 and thermal energy sensor 124 are disposed on the same side of media path P, and that system 50 employs a reference surface in the form of a keyed shield such as rotating slotted cylinder 56. As will be appreciated upon reading further, rotating slotted cylinder 56 accommodates use of temperature sensing devices which sense changes in temperature even where the thermal energy source is not pulsed. Accordingly, the depicted rotating slotted cylinder accommodates use of temperature sensing devices such as a passive infrared (PIR) sensor, or a polyvinylidene fluoride (PVDF) sensor, both of which sense temperature changes.

As indicated, slotted cylinder 56, may have slots 58, reference portions 60 and an axle 62. Using axle 62, cylinder 56 may rotate about thermal sensor 124, with reference portions 60 intermittently blocking radiated heat from media sheet S so as to function as reference surfaces. Correspondingly, slots 58 intermittently allow sensing of media sheet S so as to give the effect of interleaved heated patches and unheated reference patches passing by thermal sensor 124. Because reference portions 60 of cylinder 56 function as a reference surface, it may be desirable that cylinder 56 be formed of a material having an emissivity near unity, for reasons previously described. Slotted cylinder 56 may rotate in concert with feed roller 14 as media sheet S is fed along feed path P, thereby coordinating passage of media sheet S with rotation of slotted cylinder 56. Accordingly, using similar methodology to that described above, heat capacity of media sheet S may be determined, and correspondingly, system 50 may be used to identify media weight and media type.

While the present invention has been particularly shown and described with reference to the foregoing preferred embodiments, those skilled in the art will understand that many variations may be made therein without departing from the spirit and scope of the invention as defined in the following claims. The description of the invention should be understood to include all novel and non-obvious combinations of elements described herein, and claims may be presented in this or a later application to any novel and non-obvious combination of these elements. The foregoing embodiments are illustrative, and no single feature or element is essential to all possible combinations that may be claimed in this or a later application. Where the claims recite "a" or "a first" element or the equivalent thereof, such claims should be understood to include incorporation of one or more such elements, neither requiring nor excluding two or more such elements.

What is claimed is:

1. A media processing device comprising:
   a media feed mechanism configured to pass media downstream along a media feed path;
   a heat source disposed along the feed path to heat media passing downstream along the media feed path, the heat source being a pulsed heat source configured to produce interleaved heated patches and unheated reference patches on the media;
   a temperature sensor disposed along the feed path downstream from the heat source, the temperature sensor being configured to sense temperature of media passing downstream from the heat source, whereby sensing of such heated patches and unheated reference patches by the temperature sensor produces a waveform representative of heat capacity of the media; and
   a processor coupled with the temperature sensor to selectively identify media type based on sensed temperature of the media.

2. The media processing device of claim 1, wherein the processor is configured to receive the waveform representative of heat capacity of the media, such heat capacity being indicative of media type.

3. A method of determining media type, the method comprising:
   applying thermal energy to media, wherein applying thermal energy includes pulsing thermal energy from a heat source towards the media to produce interleaved heated and unheated patches of media;
   feeding the media downstream along a media feed path;
   sensing thermal energy radiated from the media, such heated and unheated patches being sensed by a temperature sensor to produce a waveform representative of heat capacity of the media; and
   calculating a heat capacity of the media based on the thermal energy radiated from the media.

4. The method of claim 3, wherein calculating a heat capacity of the media includes performing a root mean square operation on the waveform.

5. A media processing device comprising:
   media feed means configured to pass media downstream along a media feed path;
   heating means disposed along the feed path for applying thermal energy to media passing downstream alone the media feed path;
   temperature-sensing means disposed along the feed path downstream from the heat source for selectively sensing temperature of media passing downstream from the heating means; and
   a processor means coupled with the temperature-sensing means for receiving an output representative of the sensed temperature, determining heat capacity of the media based on such output, and identifying media type based on such heat capacity, wherein the processor means is configured to determine heat capacity based a root mean square calculation performed on an output representative of the sensed temperature.

\* \* \* \* \*

UNITED STATES PATENT AND TRADEMARK OFFICE
CERTIFICATE OF CORRECTION

PATENT NO. : 6,726,357 B2  Page 1 of 1
DATED : April 27, 2004
INVENTOR(S) : Phillip R. Luque et al.

It is certified that error appears in the above-identified patent and that said Letters Patent is hereby corrected as shown below:

Column 1,
Line 59, after "FIG. 1" insert -- . --

Column 6,
Line 49, delete "alone" and insert therefor -- along --
Line 61, after "based" insert -- on --

Signed and Sealed this

Eleventh Day of January, 2005

JON W. DUDAS
*Director of the United States Patent and Trademark Office*